(12) United States Patent
Ree et al.

(10) Patent No.: US 10,907,068 B2
(45) Date of Patent: Feb. 2, 2021

(54) CELL MEMBRANE-MIMICKING BRUSH POLYMER AND METHOD FOR PREPARDING SAME

(71) Applicants: CEKO CO., LTD., Gyeonggi-do (KR); POSTECH ACADEMY-INDUSTRY FOUNDATION, Gyeongsangbuk-do (KR)

(72) Inventors: Moon-Hor Ree, Gyeongsangbuk-do (KR); Kyung-Ho Kwon, Daegu (KR); Jong-Chan Lee, Jeollanam-do (KR); Chang-Sub Kim, Chungcheongnam-do (KR); Hyun-Joong Kim, Seoul (KR); Hong-Chul Kim, Seoul (KR); Jeong-Rae Kim, Seoul (KR)

(73) Assignees: CEKO CO., LTD., Gyeonggi-do (KR); POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 105 days.

(21) Appl. No.: 16/349,849

(22) PCT Filed: Nov. 7, 2017

(86) PCT No.: PCT/KR2017/012538
§ 371 (c)(1),
(2) Date: May 14, 2019

(87) PCT Pub. No.: WO2018/088775
PCT Pub. Date: May 17, 2018

(65) Prior Publication Data
US 2019/0276701 A1 Sep. 12, 2019

(30) Foreign Application Priority Data
Nov. 14, 2016 (KR) .................. 10-2016-0151218

(51) Int. Cl.
| | | |
|---|---|---|
| C09D 171/08 | (2006.01) | |
| C08G 65/26 | (2006.01) | |
| G01N 33/15 | (2006.01) | |
| G01N 33/50 | (2006.01) | |
| G01N 33/92 | (2006.01) | |
| C09D 171/00 | (2006.01) | |
| G01N 33/543 | (2006.01) | |

(52) U.S. Cl.
CPC ........... *C09D 171/08* (2013.01); *C08G 65/26* (2013.01); *C09D 171/00* (2013.01); *G01N 33/15* (2013.01); *G01N 33/5076* (2013.01); *G01N 33/92* (2013.01); *G01N 33/54393* (2013.01)

(58) Field of Classification Search
CPC .... C09D 171/08; C09D 171/00; C08G 65/26; G01N 33/15; G01N 33/5076; G01N 33/92; G01N 33/54393
See application file for complete search history.

(56) References Cited

FOREIGN PATENT DOCUMENTS

| | | |
|---|---|---|
| KR | 10-0798596 B1 | 1/2008 |
| KR | 10-0934125 B1 | 12/2009 |
| KR | 10-2010-0078325 A | 7/2010 |
| KR | 10-2010-0093404 A | 8/2010 |
| KR | 10-2015-0080424 A | 7/2015 |

OTHER PUBLICATIONS

International Search Report from corresponding PCT Application No. PCT/KR2017/012538, dated Feb. 8, 2018, with English translation.

*Primary Examiner* — Shane Fang
(74) *Attorney, Agent, or Firm* — Harness, Dickey & Pierce, P.L.C.

(57) ABSTRACT

The present invention relates to a cell membrane-mimicking brush polymer having surface properties mimicking a cell membrane and a self-assembly capability by means of a cell membrane mimicking functional group introduced to a brush terminal, and a method for preparing same.

9 Claims, 6 Drawing Sheets

CELL MEMBRANE-MIMICKING BRUSH POLYMER AND METHOD FOR PREPARING SAME

CROSS-REFERENCE TO RELATED APPLICATIONS

This application is a national phase application of PCT Application No. PCT/KR2017/012538, filed on Nov. 7, 2017, which claims the benefit and priority to Korean Patent Application No. 10-2016-0151218, filed on Nov. 14, 2016. The entire disclosures of the applications identified in this paragraph are incorporated herein by references.

FIELD

The present invention relates to a cell membrane-mimicking brush polymer and a method for preparing the same.

BACKGROUND

Research on the introduction of functional molecules targeting biocompatibility, specific molecules, proteins and cells through various polymer materials mimicking cell membranes and surface control methods is actively under way. Particularly, in the case of protein adsorption experiments using the surface plasmon resonance method, a method using self-assembled monolayers (SAMs) is most widely used. SAMs can realize desired surface characteristics by introducing monomolecules having self-assembling properties onto the substrate surface. In particular, it has been applied to biosensor research for tracking specific molecules and proteins, and research of a surface having biocompatibility using monomolecules having various biomolecules.

However, since SAMs have limitations on chemical stability and structure, they have a fatal problem in deepening research and applications.

DISCLOSURE

Technical Purpose

The purpose of the present invention is to provide a cell membrane-mimicking brush polymer having a self-assembly capability and surface properties mimicking a cell membrane by using a cell membrane-mimicking functional group introduced to a brush terminal, and a method for preparing the same.

Technical Solution

In order to achieve the technical purpose, the present invention provides a brush polymer compound comprising a structure represented by the following Formula 1:

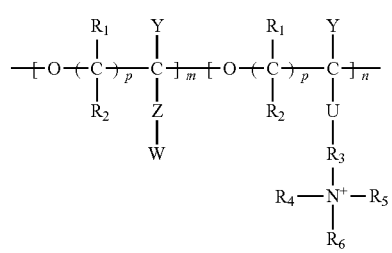

[Formula 1]

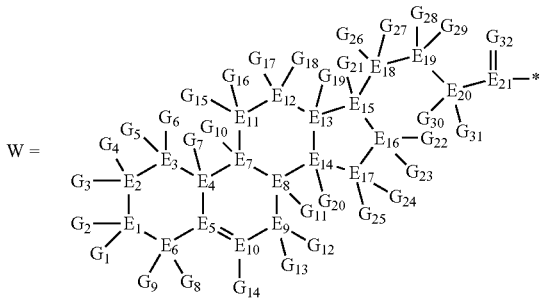

[Formula 2]

wherein, $R_1$, $R_2$, $R_4$, $R_5$ and $R_6$ are independently hydrogen or an alkyl group having 1 to 20 carbon atoms; $R_3$ is an alkylene having 1 to 20 carbon atoms; $\rho$ is an integer of 0 to 20; m and n represent the content (mol %) of the polyether unit, $0 \leq m \leq 100$, $0 \leq n \leq 100$ and m+n=100;

Y is H, —$CH_2X$ (wherein X is F, Cl, Br or I), an alkyl group having 1 to 20 carbon atoms, $UR_3N^{\oplus}[R_4R_5R_6]$ or —ZW;

Z and U are linkers connecting the terminal functional group and the polyether backbone;

W is a carbocyclic group of the Formula 2 comprising $E_1$ to $E_{21}$ and $G_1$ to $G_{32}$;

-* represents the point to be connected to Z;

$E_1$ to $E_{21}$ are independently selected from the group consisting of C, N, O, P and S;

provided that $E_4$, $E_5$, $E_7$, $E_8$, $E_{10}$, $E_{13}$, $E_{14}$ and $E_{15}$ are not O and S;

when any one of $E_1$ to $E_{21}$ is O or S, G attached thereto is not present;

when any one of $E_1$ to $E_{21}$ is N or P, there is no or at most one G attached thereto;

$G_1$ to $G_{32}$, when present, are independently selected from the group consisting of —CHO, COOH, —H, —$N_3$, —$NO_2$, —$NH_2$, —OH, —$PO_3H$, —SH, —$SO_3H$, —$CH_3$, —$C_6H_5$ and alkyl group having 1 to 20 carbon atoms, or together form =O, =N or =S with two G's connected to the same E.

In the second aspect, the present invention provides a method for preparing a brush polymer compound, comprising the steps of:

step (1) of preparing a polyether polymer compound comprising a structure represented by the Formula 6 from the cyclic monomers of the Formula 5 through cationic ring-opening polymerization, step (2) of preparing a polymer compound having an azide group and comprising a structure represented by the Formula 7 from the polyether polymer comprising the structure of the Formula 6 in the step (1) through a halogen substitution reaction in an organic solvent and step (3) of preparing a brush polymer compound of the Formula 1 using the azide group of the polymer compound having an azide group of the step (2) and the cycloaddition reaction of the alkyne group of the functional molecule:

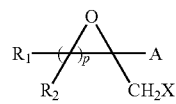

[Formula 5]

-continued

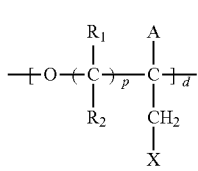
[Formula 6]

in the Formulas 5 and 6, $R_1$ and $R_2$ are hydrogen or an alkyl group having 1 to 20 carbon atoms, $\rho$ is an integer of 0 to 20, d is 50 to 50,000, A is hydrogen, an alkyl group having 1 to 20 carbon atoms or —$CH_2X$ (wherein X is F, Cl, Br or I),

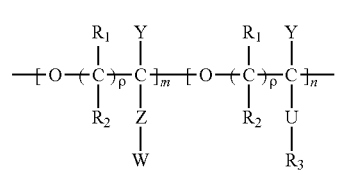
[Formula 7]

in the Formula 7, $R_1$ and $R_2$ are hydrogen or an alkyl group having 1 to 20 carbon atoms, $\rho$ is an integer of 0 to 20, d is 50 to 50,000 and A' is H, —$CH_2N_3$ or an alkyl group having 1 to 20 carbon atoms,

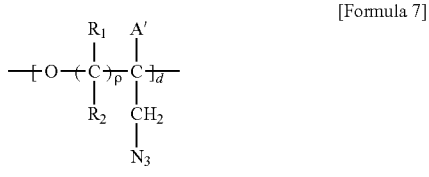
[Formula 1]

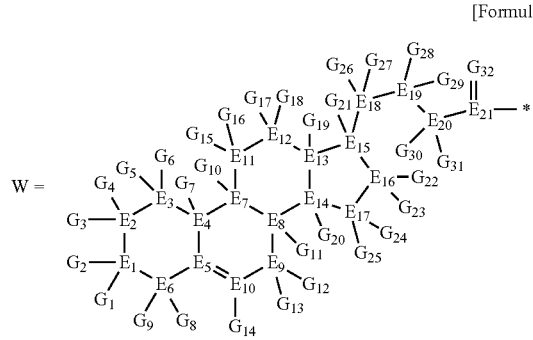
[Formula 2]

wherein,
$R_1$, $R_2$, $R_4$, $R_5$ and $R_6$ are independently hydrogen or an alkyl group having 1 to 20 carbon atoms; $R_3$ is an alkylene having 1 to 20 carbon atoms; $\rho$ is an integer of 0 to 20; m and n represent the content (mol %) of the polyether unit, $0 \leq m \leq 100$, $0 \leq n \leq 100$ and m+n=100;
Y is H, —$CH_2X$ (wherein X is F, Cl, Br or I), an alkyl group having 1 to 20 carbon atoms, $UR_3N^{\oplus}[R_4R_5R_6]$ or —ZW;
Z and U are linkers connecting the terminal functional group and the polyether backbone;
W is a carbocyclic group of the Formula 2 comprising $E_1$ to $E_{21}$ and $G_1$ to $G_{32}$;

-* represents the point to be connected to Z;
$E_1$ to $E_{21}$ are independently selected from the group consisting of C, N, O, P and S;
provided that $E_4$, $E_5$, $E_7$, $E_8$, $E_{10}$, $E_{13}$, $E_{14}$ and $E_{15}$ are not O and S;
when any one of $E_1$ to $E_{21}$ is O or S, G attached thereto is not present;
when any one of $E_1$ to $E_{21}$ is N or P, there is no or at most one G attached thereto;
$G_1$ to $G_{32}$, when present, are independently selected from the group consisting of —CHO, COOH, —H, —$N_3$, —$NO_2$, —$NH_2$, —OH, —$PO_3H$, —SH, —$SO_3H$, —$CH_3$, —$C_6H_5$ and alkyl group having 1 to 20 carbon atoms, or together form =O, =N or =S with two G's connected to the same E; and
the functional molecule comprises $UR_3N^{\oplus}[R_4R_5R_6]$ or —ZW at either end, and comprises an alkyne group at the opposite end.

In the third aspect, the present invention provides a polymer thin film comprising the above brush polymer compound.

In the fourth aspect, the present invention provides a method for preparing a polymer thin film, which comprises a step of coating the above brush polymer compound on a substrate.

In the fifth aspect, the present invention provides a method for preparing a polyether polymer compound comprising a structure represented by the Formula 6, comprising a step of conducting a cationic ring-opening polymerization reaction using the cyclic monomer of the Formula 5 as a reactant:

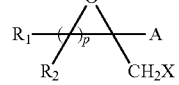
[Formula 5]

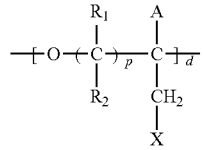
[Formula 6]

in the Formulas 5 and 6, $R_1$ and $R_2$ are hydrogen or an alkyl group having 1 to 20 carbon atoms, $\rho$ is an integer of 0 to 20, d is 50 to 50,000, A is hydrogen, an alkyl group having 1 to 20 carbon atoms or —$CH_2X$ (wherein X is F, Cl, Br or I).

In the sixth aspect, the present invention provides a method for preparing a polymer compound having an azide group and comprising a structure represented by the Formula 7, comprising a step of conducting a halogen substitution reaction in an organic solvent from the polyether polymer comprising the structure of the Formula 6 as a reactant:

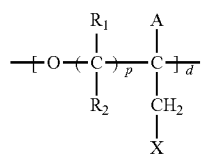
[Formula 6]

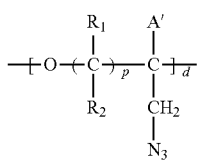

[Formula 7]

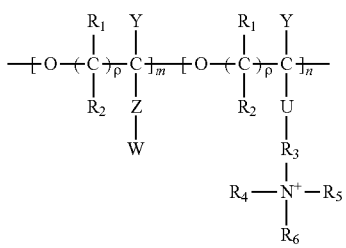

[Formula 1]

in the Formulas 6 and 7, $R_1$ and $R_2$ are hydrogen or an alkyl group having 1 to 20 carbon atoms, $\rho$ is an integer of 0 to 20, d is 50 to 50,000, A is hydrogen, an alkyl group having 1 to 20 carbon atoms or —$CH_2X$ (wherein X is F, Cl, Br or I) and A' is H, —$CH_2N_3$ or an alkyl group having 1 to 20 carbon atoms.

Advantageous Effects

According to the present invention, it is possible to overcome the disadvantages of the SAMs described above and to form an economical polymer thin film having excellent surface control characteristics, and to provide a functional polymer substance that inhibits or prevents adhesion, adsorption and binding of various kinds of pathogenic bacteria and various blood proteins and platelets, and at the same time, selectively responds to a specific protein. A cell membrane-mimicking brush polymer can be capable of efficiently culturing the cells and micro-organisms, and it may be applied as a biocompatible material for attaching or separating particular proteins.

DETAILED DESCRIPTION

Figure 1:
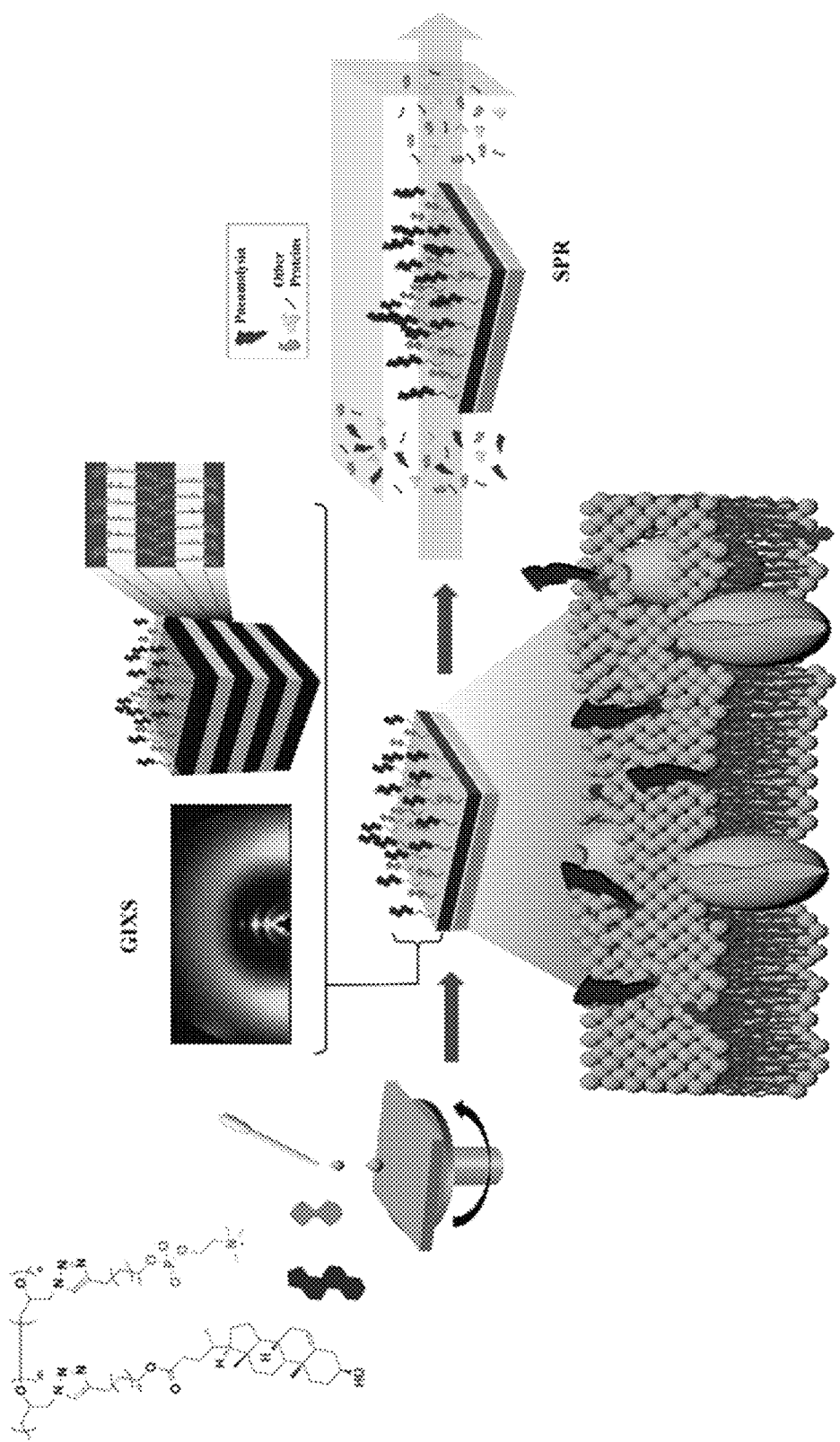
FIG. 1 is a schematic view of a method for preparing a polymer thin film of the present invention.

The present invention will be described in detail in below.

A brush polymer compound of the present invention comprises a structure represented by the following Formula 1. Since it has a cell membrane-mimicking functional group introduced to a brush terminal, it is possible to overcome the disadvantages of the SAMs described above and to form an economical polymer thin film having excellent surface control characteristics, and to provide a functional polymer substance that inhibits or prevents adhesion, adsorption and binding of various kinds of pathogenic bacteria and various blood proteins and platelets, and at the same time, selectively responds to a specific protein.

[Formula 2]

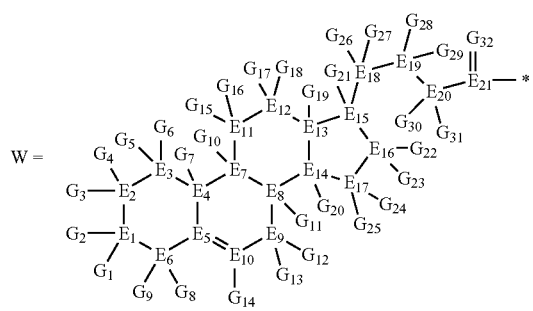

wherein, $R_1$, $R_2$, $R_4$, $R_5$ and $R_6$ are independently hydrogen or an alkyl group having 1 to 20 carbon atoms, and preferably the alkyl group having 1 to 20 carbon atoms may be an alkyl group having 1 to 15 carbon atoms, more preferably an alkyl group having 1 to 10 carbon atoms. $R_3$ is an alkylene having 1 to 20 carbon atoms, preferably having 1 to 15 carbon atoms, and more preferably having 1 to 10 carbon atoms.

$\rho$ is an integer of 0 to 20, preferably an integer of 0 to 15, and more preferably an integer of 0 to 10.

m and n represent the content (mol %) of the polyether unit, $0 \leq m \leq 100$, $0 \leq n \leq 100$ and $m+n=100$;

Y is H, —$CH_2X$ (wherein X is F, Cl, Br or I), an alkyl group having 1 to 20 carbon atoms (preferably having 1 to 15 carbon atoms, and more preferably having 1 to 10 carbon atoms), $UR_3N^{\oplus}[R_4R_5R_6]$ or —ZW;

Z and U are linkers connecting the terminal functional group and the polyether backbone;

W is a carbocyclic group of the Formula 2 comprising $E_1$ to $E_{21}$ and $G_1$ to $G_{32}$;

-* represents the point to be connected to Z;

$E_1$ to $E_{21}$ are independently selected from the group consisting of C, N, O, P and S; provided that $E_4$, $E_5$, $E_7$, $E_8$, $E_{10}$, $E_{13}$, $E_{14}$ and $E_{15}$ are not O and S;

when any one of $E_1$ to $E_{21}$ is O or S, G attached thereto is not present;

when any one of $E_1$ to $E_{21}$ is N or P, there is no or at most one G attached thereto;

$G_1$ to $G_{32}$, when present, are independently selected from the group consisting of —CHO, COOH, —H, —$N_3$, —$NO_2$, —$NH_2$, —OH, —$PO_3H$, —SH, —$SO_3H$, —$CH_3$, —$C_6H_5$ and alkyl group having 1 to 20 carbon atoms (preferably having 1 to 15 carbon atoms, and more preferably having 1 to 10 carbon atoms), or together form =O, =N or =S with two G's connected to the same E.

Z and U are linkers connecting the terminal functional group and the polyether backbone; and are independently selected from the group represented by the following Formula 3:

[Formula 3]
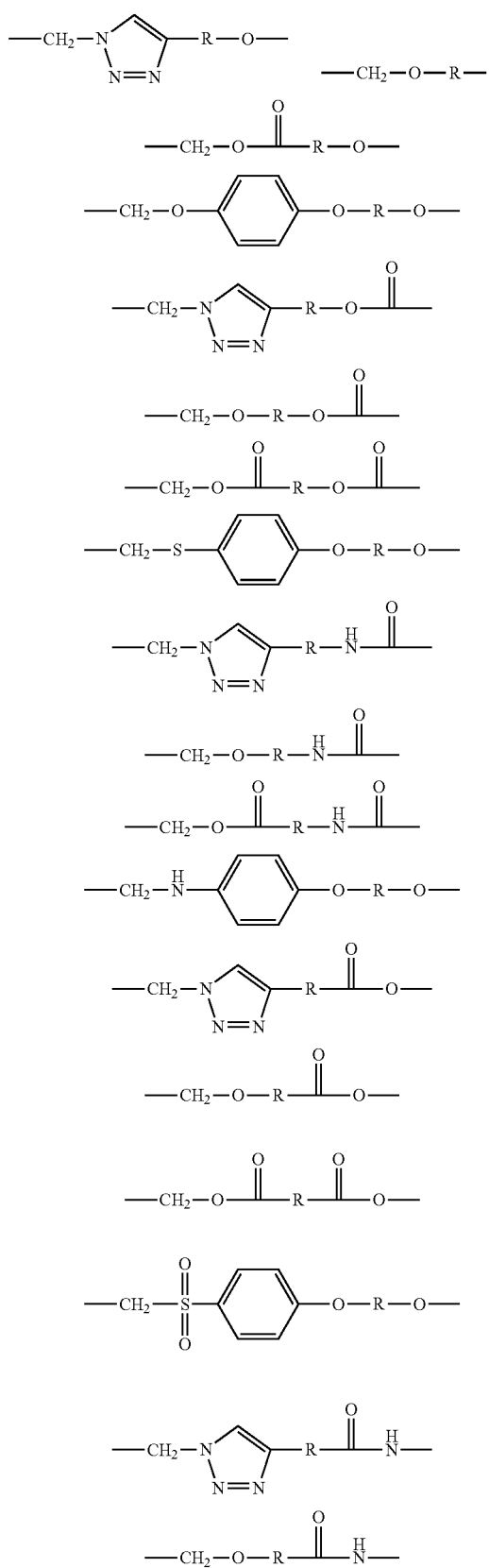
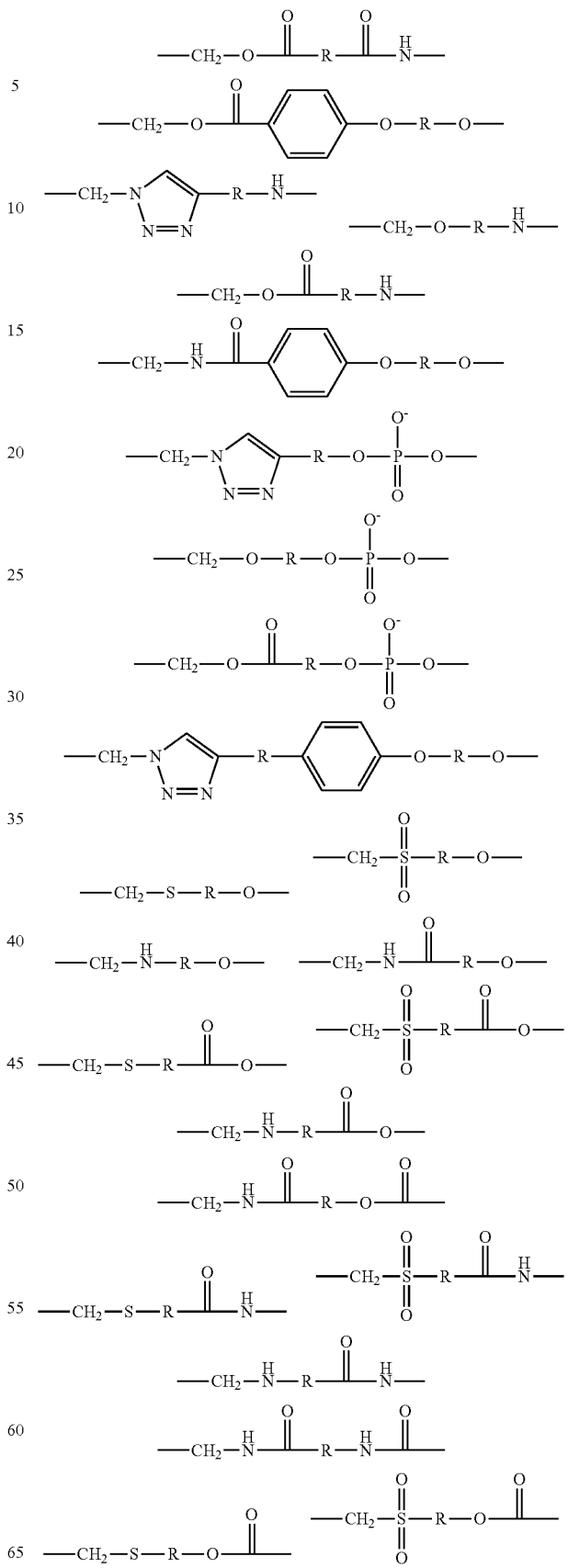

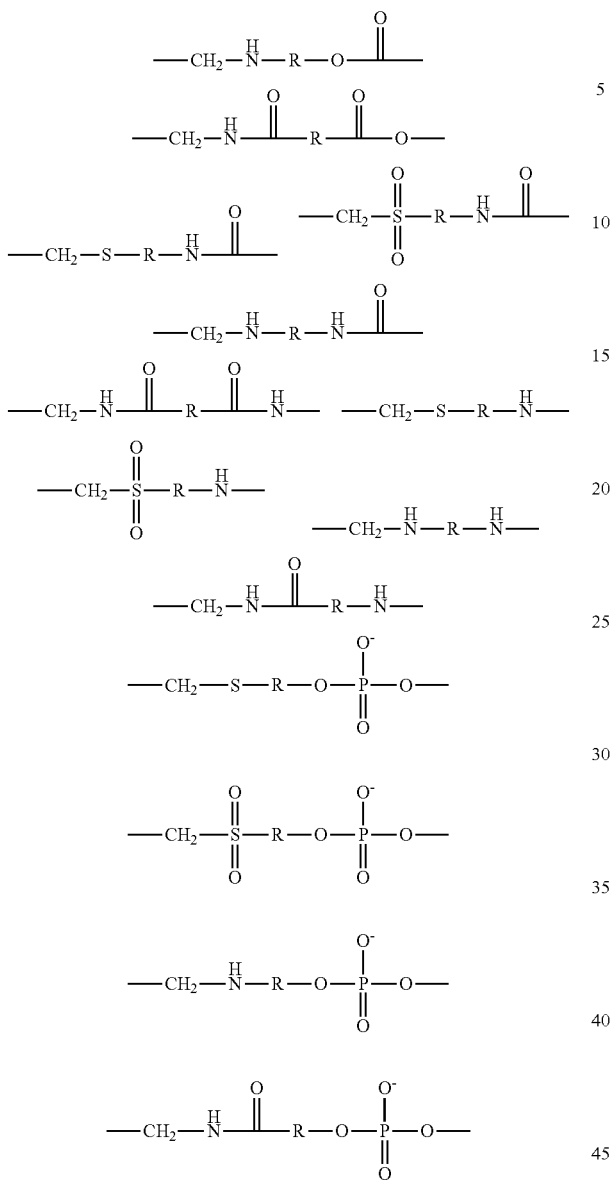

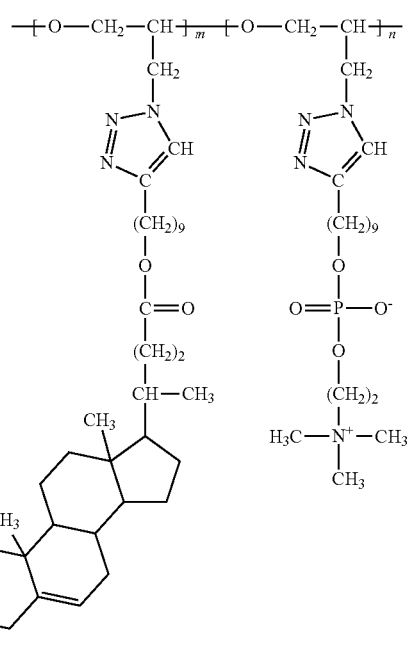

wherein R is hydrogen or an alkylene group having 1 to 20 carbon atoms (preferably having 1 to 15 carbon atoms, and more preferably having 1 to 10 carbon atoms).

The brush polymer compound of the present invention may have a weight average molecular weight of 5,000 to 5,000,000, preferably 5,000 to 500,000. When the weight average molecular weight is too small, there is a problem in the stability of the polymer thin film. On the other hand, when the weight average molecular weight is too large, there is a problem in solubility in an organic solvent.

In one embodiment of the present invention, the brush polymer compound is a poly [oxy(4-(14-cholenoatenonyl)-1,2,3-triazol-1-methyl)ethylene-lan-oxy(4-(14-phosphorylcolynylnonyl)-1,2,3-triazol-1-methyl)ethylene] (hereinafter abbreviated as PGA-CholmPCn), comprising a structure represented by the following Formula 4:

wherein m and n represent the content (mol %) of the polyether unit, $0 \leq m \leq 100$, $0 \leq n \leq 100$ and $m+n=100$.

In another aspect, the present invention provides a method for preparing a brush polymer compound, comprising the steps of:

step (1) of preparing a polyether polymer compound comprising a structure represented by the Formula 6 from the cyclic monomers of the Formula 5 through cationic ring-opening polymerization, step (2) of preparing a polymer compound having an azide group and comprising a structure represented by the Formula 7 from the polyether polymer comprising the structure of the Formula 6 in the step (1) through a halogen substitution reaction in an organic solvent and step (3) of preparing a brush polymer compound of Formula 1 using the azide group of the polymer compound having an azide group of the step (2) and the cycloaddition reaction of the alkyne group of the functional molecule:

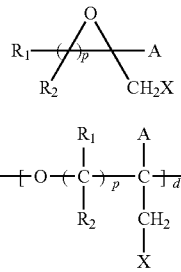

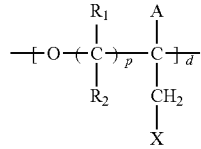

in the Formulas 5 and 6, $R_1$ and $R_2$ are hydrogen or an alkyl group having 1 to 20 carbon atoms, $p$ is an integer of 0 to 20, d is 50 to 50,000, A is hydrogen, an alkyl group having 1 to 20 carbon atoms or —CH$_2$X (wherein X is F, Cl, Br or I),

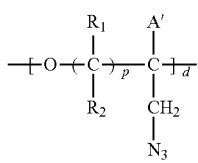

[Formula 7]

in the Formula 7, $R_1$ and $R_2$ are hydrogen or an alkyl group having 1 to 20 carbon atoms, $\rho$ is an integer of 0 to 20, d is 50 to 50,000 and A' is H, —CH$_2$N$_3$ or an alkyl group having 1 to 20 carbon atoms,

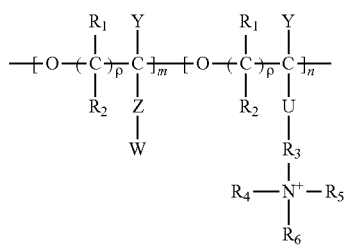

[Formula 1]

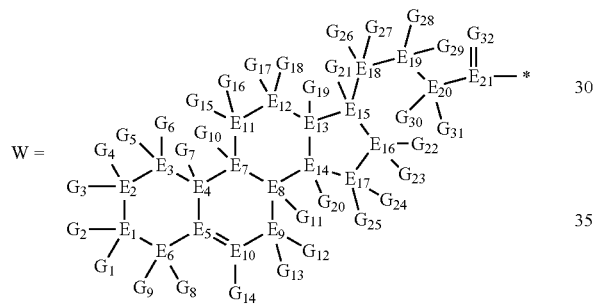

[Formula 2]

wherein,
$R_1$, $R_2$, $R_4$, $R_5$ and $R_6$ are independently hydrogen or an alkyl group having 1 to 20 carbon atoms; $R_3$ is an alkylene having 1 to 20 carbon atoms; $\rho$ is an integer of 0 to 20; m and n represent the content (mol %) of the polyether unit, 0≤m≤100, 0≤n≤100 and m+n=100;
Y is H, —CH$_2$X (wherein X is F, Cl, Br or I), an alkyl group having 1 to 20 carbon atoms, UR$_3$N$^\oplus$[R$_4$R$_5$R$_6$] or —ZW;
Z and U are linkers connecting the terminal functional group and the polyether backbone;
W is a carbocyclic group of the Formula 2 comprising $E_1$ to $E_{21}$ and $G_1$ to $G_{32}$;
-* represents the point to be connected to Z;
$E_1$ to $E_{21}$ are independently selected from the group consisting of C, N, O, P and S; provided that $E_4$, $E_5$, $E_7$, $E_8$, $E_{10}$, $E_{13}$, $E_{14}$ and $E_{15}$ are not O and S;
when any one of $E_1$ to $E_{21}$ is O or S, G attached thereto is not present;
when any one of $E_1$ to $E_{21}$ is N or P, there is no or at most one G attached thereto;
$G_1$ to $G_{32}$, when present, are independently selected from the group consisting of —CHO, COOH, —H, —N$_3$, —NO$_2$, —NH$_2$, —OH, —PO$_3$H, —SH, —SO$_3$H, —CH$_3$, —C$_6$H$_5$ and alkyl group having 1 to 20 carbon atoms, or together form =O, =N or =S with two G's connected to the same E; and the functional molecule comprises UR$_3$N$^\oplus$[R$_4$R$_5$R$_6$] or —ZW at either end, and comprises an alkyne group at the opposite end.

In step (1), a polyether polymer compound comprising a structure represented by the Formula 6 can be prepared from the cyclic monomers of the Formula 5 through cationic ring-opening polymerization. The polyether polymer compound comprising a structure represented by the Formula 6 is an intermediate synthesized in the process of preparing the brush polymer compound of the present invention. Although not particularly limited, the cationic ring-opening polymerization reaction is a polymerization process through ring-opening reaction of epichlorohydrin, which is a cyclic monomer using triphenylcarbenium hexafluorophosphate (TCHP) as an initiator, and the reaction may be carried out by stirring the reactants in a nitrogen atmosphere for 40 to 50 hours.

In one embodiment of the present invention, the polyether polymer compound comprising a structure represented by the Formula 6 can be prepared by a known method and may be prepared by conducting the cationic ring-opening polymerization reaction in the presence of a cationic initiator such as triphenylcarbenium hexafluorophosphate, triphenylcarbenium hexachloroantimonate, alkylaluminum or etc.

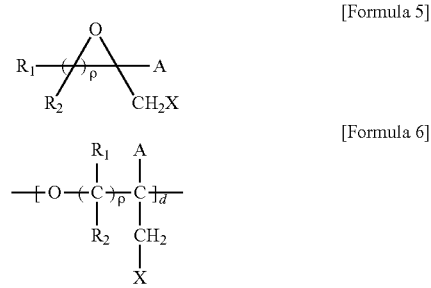

[Formula 5]

[Formula 6]

in the Formulas 5 and 6, $R_1$ and $R_2$ are hydrogen or an alkyl group having 1 to 20 carbon atoms (preferably having 1 to 15 carbon atoms, and more preferably having 1 to 10 carbon atoms), $\rho$ is an integer of 0 to 20, d is 50 to 50,000, A is hydrogen, an alkyl group having 1 to 20 carbon atoms (preferably having 1 to 15 carbon atoms, and more preferably having 1 to 10 carbon atoms) or —CH$_2$X (wherein X is F, Cl, Br or I).

In step (2), a polymer compound having an azide group and comprising a structure represented by the Formula 7 can be prepared from the polyether polymer comprising the structure of the Formula 6 in the step (1) through a halogen substitution reaction in an organic solvent. The polymer compound having an azide group and comprising a structure represented by the Formula 7 is an intermediate synthesized in the process of preparing the brush polymer compound of the present invention.

In one embodiment of the present invention, the halogen substitution reaction can introduce an azide (—N3) group by reacting a CH2X group with sodium azide (NaN3). Examples of the organic solvent include, but are not limited to, dimethylacetamide, dimethylformamide or a mixed solution thereof.

The reaction in step (2) may be conducted at a temperature of −100 to 100° C. and a pressure of 1 to 5 atm.

[Formula 7]

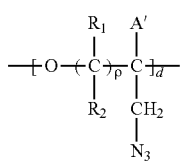

in the Formula 7, $R_1$ and $R_2$ are hydrogen or an alkyl group having 1 to 20 carbon atoms (preferably having 1 to 15 carbon atoms, and more preferably having 1 to 10 carbon atoms), $\rho$ is an integer of 0 to 20, d is 50 to 50,000 and A' is H, —$CH_2N_3$ or an alkyl group having 1 to 20 carbon atoms (preferably having 1 to 15 carbon atoms, and more preferably having 1 to 10 carbon atoms).

In step (3), a brush polymer compound of Formula 1 can be prepared using the azide group of the polymer compound having an azide group of the step (2) and the cycloaddition reaction of the alkyne group of the functional molecule.

The functional molecule used in the cycloaddition reaction comprises UR3N⊕[R4R5R6] or —ZW at either end, and comprises an alkyne group at the opposite end,
  wherein $R_4$, $R_5$ and $R_6$ are independently hydrogen or an alkyl group having 1 to 20 carbon atoms (preferably having 1 to 15 carbon atoms, and more preferably having 1 to 10 carbon atoms); $R_3$ is an alkylene having 1 to 20 carbon atoms (preferably having 1 to 15 carbon atoms, and more preferably having 1 to 10 carbon atoms);
  Z and U are linkers connecting the terminal functional group and the polyether backbone;
  W is a carbocyclic group of the Formula 2 comprising $E_1$ to $E_{21}$ and $G_1$ to $G_{32}$;
  -* represents the point to be connected to Z;
  $E_1$ to $E_{21}$ are independently selected from the group consisting of C, N, O, P and S;
  provided that $E_4$, $E_5$, $E_7$, $E_8$, $E_{10}$, $E_{13}$, $E_{14}$ and $E_{15}$ are not O and S;
  when any one of $E_1$ to $E_{21}$ is O or S, G attached thereto is not present;
  when any one of $E_1$ to $E_{21}$ is N or P, there is no or at most one G attached thereto;
  $G_1$ to $G_{32}$, when present, are independently selected from the group consisting of —CHO, COOH, —H, —$N_3$, —$NO_2$, —$NH_2$, —OH, —$PO_3H$, —SH, —$SO_3H$, —$CH_3$, —$C_6H_5$ and alkyl group having 1 to 20 carbon atoms, or together form =O, =N or =S with two G's connected to the same E.

The cycloaddition reaction (Cu(I)-Catalyzed Azide-Alkyne Cycloaddition) is a cycloaddition reaction of azide and alkyne groups. As the solvent, dimethylacetamide, dimethylformamide, diethyl ether, dichloromethane, tetrahydrofuran or a mixed solution thereof may be used, but the present invention is not limited thereto.

Another aspect of the present invention provides a polymer thin film comprising the above brush polymer compound. Another aspect of the present invention provides a method for preparing a polymer thin film, which comprises a step of coating the above brush polymer compound on a substrate.

The brush polymer compound may be coated by any method selected from the group consisting of spin coating, spray coating, electrostatic coating, dip coating, blade coating, ink jet coating and roll coating.

The method for preparing a polymer thin film of the present invention comprises a step of heat treating the substrate coated with the brush polymer compound under vacuum at 30 to 100° C. for 10 to 20 hours. When out of the above temperature and time range, there is a problem in the decomposition of the polymer thin film and formation of a suitable nano-structure. At a high temperature outside the above range, decomposition of the polymer thin film may occur, and at low temperatures, there may be problems in formation of nanostructures.

BEST MODE

The present invention will be described in more detail through the Examples. However, these Examples are only intended to describe the present invention exemplarily, and the protected circumstances of the present invention are not at all limited by them.

EXAMPLE

1. Preparation of a Polyether Polymer Compound Comprising a Structure Represented by the Formula 6 (Synthesis Example 1)

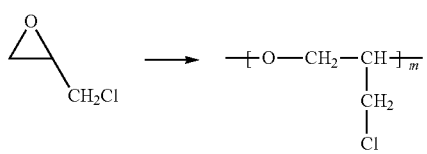

[Formula 2]

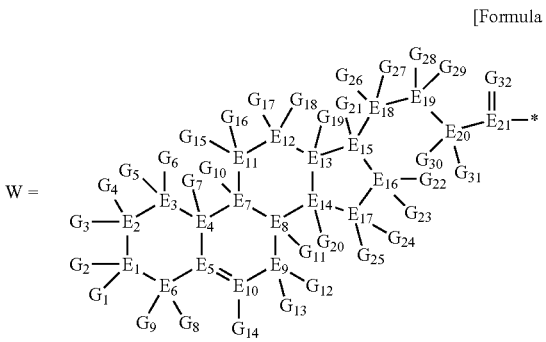

40 mL (512 mmol) of epichlorohydrin was added to a 100 mL round bottom flask and cooled to 5° C. under a nitrogen atmosphere. A solution of 2.56 mmol of the initiator in dichloromethane was added thereto, followed by stirring at room temperature for 4 days. This reactant was dissolved in a small amount of dichloromethane, reprecipitated in methanol to be purified, and then was dried at 40° C. under vacuum for 8 hours to prepare polyepichlorohydrin, which is a polyether polymer compound comprising a structure represented by the Formula 6. Yield: 65%. $^1$H-NMR (300 MHz, CDCl$_3$): δ(ppm)=3.89-3.49 (br, 5H, —OCH—, —OCH$_2$—, —CH$_2$Cl); $^{13}$C-NMR (75 MHz, CDCl$_3$): δ(ppm)=79.70, 70.32, 44.31; FTIR(in film):ν(cm$^{-1}$)=2960, 2915, 2873, 1427, 1348, 1299, 1263, 1132, 750, 707.

2. Preparation of a Polymer Compound Having an Azide Group and Comprising a Structure Represented by the Formula 7 (Synthesis Example 2)

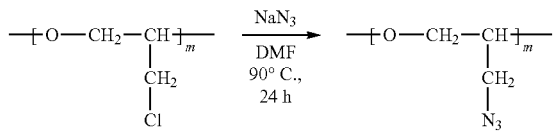

2.10 g (32.4 mmol) of sodium azide was added to a solution of 1.0 g (10.8 mmol) of the polyepichlorohydrin compound obtained from Synthesis Example 1 in 40 mL of dimethylformamide. The mixture was stirred at 90° C. for 24 hours, and dimethylformamide was removed by heating under reduced pressure. The remaining solution was extracted with chloroform, washed with water to remove the solvent, and then the solvent was removed by heating under reduced pressure. This polymer substance was dried under vacuum at 40° C. for 8 hours to obtain poly(glycidyl azide) (PGA) which is the target compound (polymer compound having an azide group and comprising a structure represented by the Formula 7). Yield: 90%. $^1$H-NMR (300 MHz, CDCl$_3$): δ(ppm)=3.78-3.63 (br, —OCH—, —OCH$_2$—), 3.50-3.32 (m, —CH$_2$N$_3$); $^{13}$C-NMR (75 MHz, CDCl$_3$): δ(ppm)=79.70, 69.60, 51.80;

3. Preparation of a Functional Molecule 1 (Synthesis Example 3)

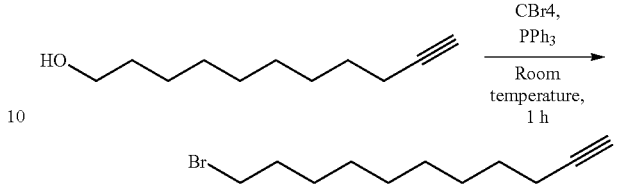

1.00 g (5.94 mmol) of 10-undecyn-1-ol and 2.17 g (6.54 mmol) of carbon tetrabromide were dissolved in dichloromethane (5 mL) together in a 100 mL round bottom flask, then 1.72 g (6.54 mmol) of triphenylphosphine was dissolved in dichloromethane (2 mL) and slowly added thereto. After stirring at room temperature for 1 hour, the reaction was terminated and the solvent was poured into cyclohexane. When precipitates were formed, the solvent was removed through a filter, and the solvent was removed by heating under reduced pressure. The remaining solution was purified by silica gel chromatography (50:1 of cyclohexane and ethyl acetate) to obtain 11-bromoundec-1-yne. Yield: 70%. $^1$H-NMR (300 MHz, CDCl$_3$): δ(ppm)=3.42 (t, 2H), 2.20 (m, 2H), 1.96 (t, 1H), 1.87 (m, 2H), 1.60-1.25 (br, 12H).

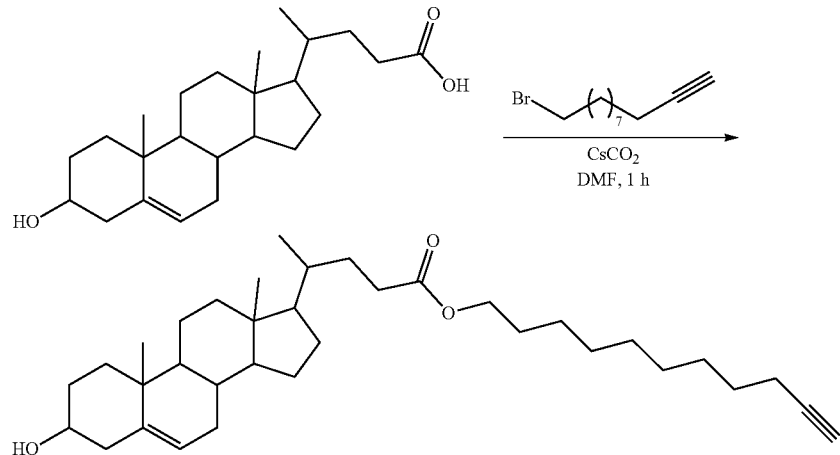

1.00 g (2.67 mmol) of 3-beta-hydroxy-delta 5-cholenic acid was dissolved in dimethylformamide (4 mL), then 1.30 g (4.00 mmol) of cesium carbonate was added and the mixture was stirred at room temperature for 1 hour. 4.01 g (16.7 mmol) of 11-bromoundec-1-yne was added thereto, and the mixture was stirred at room temperature for 20 hours. After the reaction was completed, chloroform (50 mL) was added thereto and extracted with 0.1 M HCl solution. The extracted organic solvent was dehydrated by using magnesium sulfite, and the solvent was removed by heating under reduced pressure. The resulting material was purified by silica gel chromatography (3:7 of ethyl acetate and hexane) to obtain 1-cholenoate-10-undecyne (functional molecule 1). Yield: 70%. $^1$H-NMR (300 MHz, CDCl$_3$): δ(ppm)=5.36 (m, 1H), 4.04 (t, 2H), 3.53 (m, 1H), 2.44-2.10 (m, 6H), 2.05-1.91 (m, 7H), 1.68-0.79 (m, 35H), 0.67 (s, 3H).

4. Preparation of a Functional Molecule 2 (Synthesis Example 4)

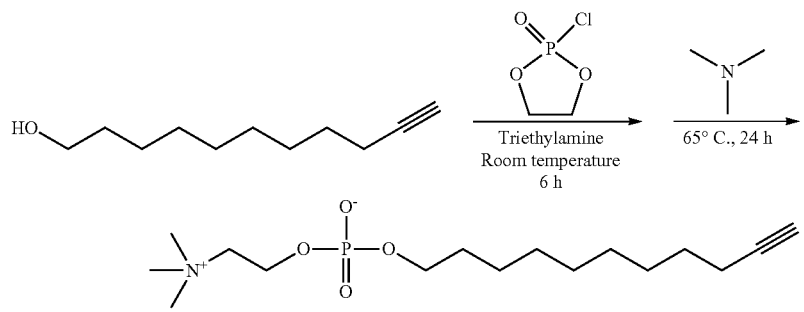

1.00 g (5.94 mol) of 10-undecyn-1-ol and 0.99 mL (6.54 mmol) of triethylamine were added to 10 mL of acetonitrile in a 100 mL round bottom flask, then the solution was cooled and stirred at 0° C. for 1 hour. 0.60 mL (6.54 mmol) of 2-chloro-2-oxa-1,3,2-dioxaphospholane was slowly added thereto, and the mixture was stirred at room temperature for 6 hours. After the completion of the reaction, the resulting precipitate was removed through a filter, and the remaining solution was cooled to 0° C. 1.76 g (30.0 mmol) of trimethylamine was added thereto and stirred at 60° C. for 24 hours. The reaction solution was kept frozen at 0° C. for 6 hours to allow precipitation. The resulting precipitate was collected through a filter, washed with acetone, and dried to prepare 10-undecynyle-1-phosphorylcholine (functional molecule 2). Yield: 65%. $^1$H-NMR (300 MHz, CDCl$_3$): δ(ppm)=4.25 (br, 2H), 3.88 (m, 2H), 3.62 (m, 2H), 3.21 (s, 9H), 2.18 (m, 3H), 1.72-1.58 (br, 2H), 1.58-1.20 (br, 12H).

5. Preparation of Brush Polymer Compound (Example 1) (m=100, n=0)

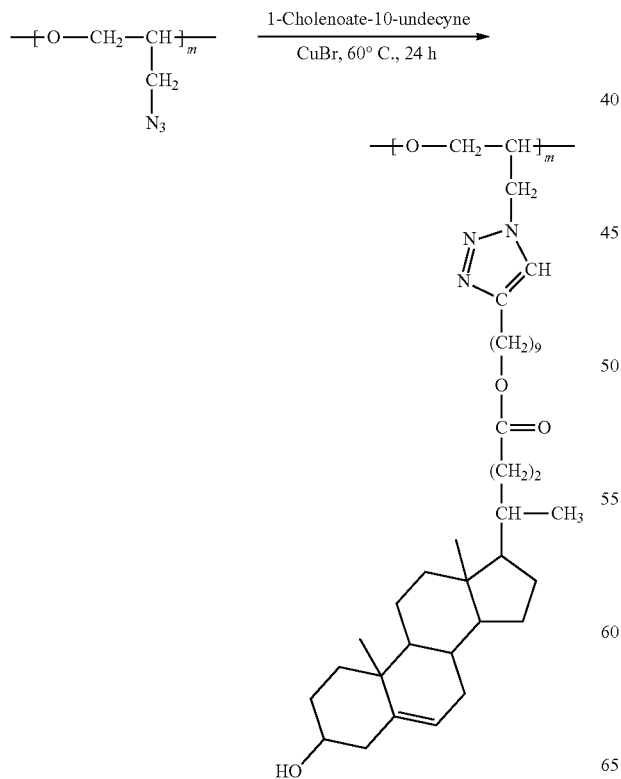

100 mg (1.00 $N_3$ mmol) of the polymer compound (PGA) obtained from Synthesis Example 2 was dissolved in dimethylsulfoxide (4 mL), and then 524 mg (1.00 mmol) of 1-cholenoate-10-undecyne was added thereto and dissolved. 7.2 mg (5 mol %) of copper bromide was added to the mixture, and the mixture was stirred at 60° C. for 24 hours. After the reaction was completed, the resultant was purified through an activated alumina filter, dissolved in a small amount of chloroform, precipitated in cold diethyl ether, and dried. The resulting precipitate was collected through a filter and vacuum-dried to obtain a brush polymer compound. $^1$H NMR (300 MHz, CDCl$_3$): δ=8.00-7.40 (br, 1H, —C=CH— in triazole), 5.36 (m, 1H, —C=CH—), 4.50-3.10 (br, 5H, —CH$_2$CHO—, —CH$_2$CHO—, —CH$_2$-Triazole in backbone), 4.04 (m, 2H, —COOCH$_2$—), 3.53 (m, 1H, —CHOH), 2.65 (m, 2H, —CH$_2$-triazole in brush linker), 2.42-2.13 (m, 4H, cholesteric acid protons, brush linker protons), 2.10-0.86 (m, 41H, cholesteric acid protons, brush linker protons), 0.71 (s, 3H, —CH$_3$). $^{13}$C NMR (150 MHz, CDCl$_3$): δ=173.96, 148.22, 141.01, 122.14, 121.34, 77.95, 71.61, 68.78, 64.21, 56.85, 56.02, 50.77, 50.32, 42.46, 42.43, 39.88, 37.39, 36.56, 35.28, 32.03, 31.89, 31.76, 31.37, 31.12, 29.47, 29.38, 29.31, 29.24, 27.99, 25.94, 25.71, 24.23, 21.13, 19.31, 18.35, 11.86.

6. Preparation of Brush Polymer Compound (Example 2) (m=75, n=25)

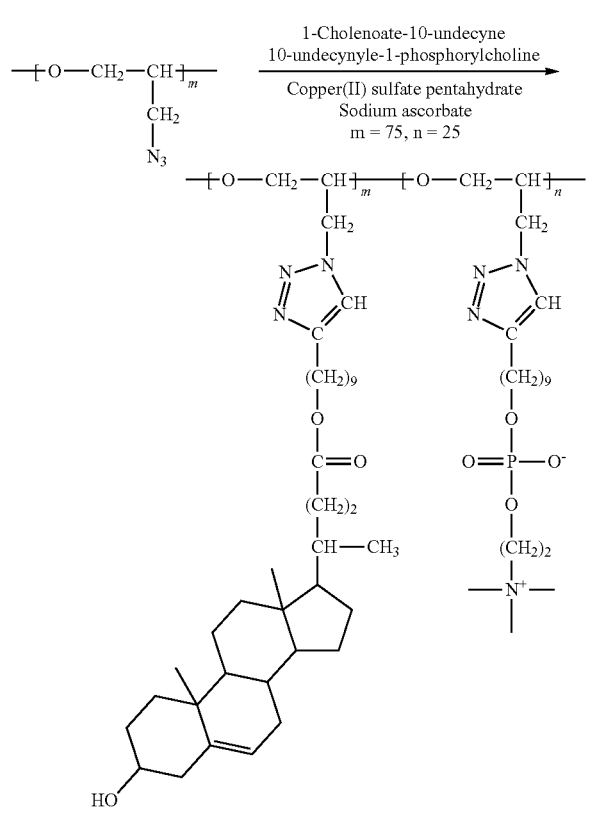

100 mg (1.00 $N_3$ mmol) of the polymer compound (PGA) obtained from Synthesis Example 2 was dissolved in a mixed solution (4 mL) of methanol and chloroform (1:3), then 397 mg (0.75 mmol) of 1-cholenoate-10-undecyne and 84 mg (0.25 mmol) of 10-undecyl-1-phosphorylcholine were added thereto and dissolved in the solution. To this mixture were added 13 mg (5 mol %) of CuSO$_4$.5H$_2$O and 30 mg (15 mol %) of sodium ascorbate, and the mixture was stirred at room temperature for 48 hours. After the reaction was completed, the reaction product was purified through dialysis and then dissolved in a small amount of chloroform/methanol mixed solution and precipitated in cold diethyl ether. The resulting precipitate was collected through a filter and vacuum-dried to obtain a brush polymer compound. $^1$H NMR (300 MHz, CD$_3$OD/CDCl$_3$): δ=8.00-7.40 (br, —C=CH— in triazole), 5.36 (m, —C=CH—), 4.50-3.10 (br, —CH$_2$CHO—, —CH$_2$CHO—, —CH$_2$-Triazole in backbone), 4.26 (m, —POCH$_2$CH$_2$N—), 4.04 (m, —COOCH$_2$—), 3.85 (m, —CH$_2$OP—), 3.67 (m, —POCH$_2$CH$_2$N—), 3.46 (m, —CHOH), 3.25 (s, —N(CH$_3$)$_3$), 2.65 (m, —CH$_2$-triazole in brush linker), 2.42-2.13 (m, cholesteric acid protons, brush linker protons), 2.10-0.85 (m, cholesteric acid protons, brush linker protons), 0.69 (s, —CH$_3$). $^{13}$C NMR (150 MHz, CD$_3$OD/CDCl$_3$): δ=174.81, 148.31, 140.90, 122.82, 121.32, 77.95, 71.13, 68.64, 66.35, 65.79, 64.46, 63.36, 58.86, 56.69, 55.73, 54.07, 50.77, 50.08, 42.31, 41.82, 39.70, 37.23, 36.44, 35.30, 31.84, 31.80, 31.24, 31.11, 30.99, 30.77, 29.50, 29.36, 29.25, 28.58, 28.03, 25.89, 25.77, 25.56, 24.17, 20.99, 19.23, 18.18, 11.74.

7. Preparation of Brush Polymer Compound (Example 3) (m=50, n=50)

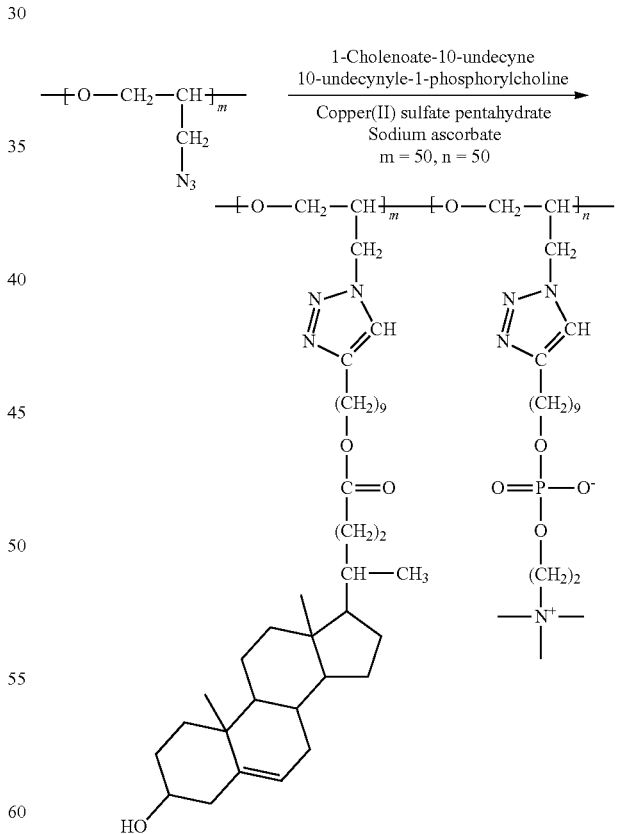

100 mg (1.00 $N_3$ mmol) of the polymer compound (PGA) obtained from Synthesis Example 2 was dissolved in a mixed solution (4 mL) of methanol and chloroform (1:3), and 262 mg (0.50 mmol) of 1-cholenoate-10-undecyne and 166 mg (0.50 mmol) of 10-undecyl-1-phosphoryl choline were added thereto and dissolved. To this mixture were added 13 mg (5 mol %) of CuSO$_4$.5H$_2$O and 30 mg (15 mol %) of sodium ascorbate, and the mixture was stirred at room temperature for 48 hours. After the reaction was completed, the reaction product was purified through dialysis and then dissolved in a small amount of chloroform/methanol mixed solution and precipitated in cold diethyl ether. The resulting precipitate was collected through a filter and vacuum-dried to obtain a brush polymer compound. $^1$H NMR (300 MHz, CD$_3$OD/CDCl$_3$): δ=8.00-7.40 (br, —C=CH— in triazole), 5.36 (m, —C=CH—), 4.50-3.10 (br, —CH$_2$CHO—, —CH$_2$CHO—, —CH$_2$-Triazole in backbone), 4.26 (m, —POCH$_2$CH$_2$N—), 4.04 (m, —COOCH$_2$—), 3.85 (m, —CH$_2$OP—), 3.67 (m, —POCH$_2$CH$_2$N—), 3.46 (m, —CHOH), 3.25 (s, —N(CH$_3$)$_3$), 2.65 (m, —CH$_2$-triazole in brush linker), 2.42-2.13 (m, cholesteric acid protons, brush linker protons), 2.10-0.85 (m, cholesteric acid protons, brush linker protons), 0.69 (s, —CH$_3$). $^{13}$C NMR (150 MHz, CD$_3$OD/CDCl$_3$): δ=174.81, 148.31, 140.90, 122.82, 121.32, 77.95, 71.13, 68.64, 66.35, 65.79, 64.46, 63.36, 58.86, 56.69, 55.73, 54.07, 50.77, 50.08, 42.31, 41.82, 39.70, 37.23, 36.44, 35.30, 31.84, 31.80, 31.24, 31.11, 30.99, 30.77, 29.50, 29.36, 29.25, 28.58, 28.03, 25.89, 25.77, 25.56, 24.17, 20.99, 19.23, 18.18, 11.74.

8. Preparation of Brush Polymer Compound (Example 4) (m=25, n=75)

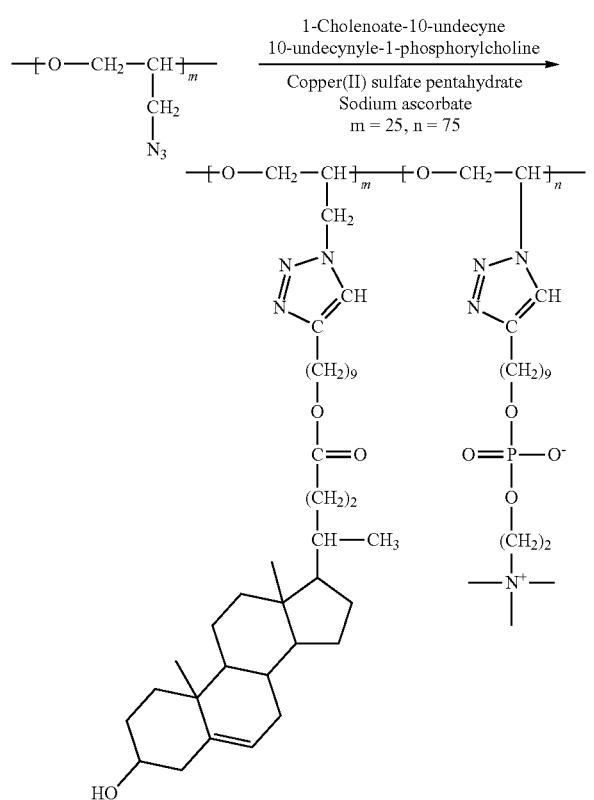

100 mg (1.00 N$_3$ mmol) of the polymer compound (PGA) obtained from Synthesis Example 2 was dissolved in a mixed solution (4 mL) of methanol and chloroform (1:3), and then 131 mg (0.25 mmol) of 1-cholenoate-10-undecyne and 250 mg (0.75 mmol) of 10-undecyl-1-phosphoryl choline were added thereto and dissolved in the solution. To this mixture were added 13 mg (5 mol %) of CuSO$_4$.5H$_2$O and 30 mg (15 mol %) of sodium ascorbate, and the mixture was stirred at room temperature for 48 hours. After the reaction was completed, the reaction product was purified through dialysis and then dissolved in a small amount of chloroform/methanol mixed solution and precipitated in cold diethyl ether. The resulting precipitate was collected through a filter and vacuum-dried to obtain a brush polymer compound. $^1$H NMR (300 MHz, CD$_3$OD/CDCl$_3$): δ=8.00-7.40 (br, —C=CH— in triazole), 5.36 (m, —C=CH—), 4.50-3.10 (br, —CH$_2$CHO—, —CH$_2$CHO—, —CH$_2$-Triazole in backbone), 4.26 (m, —POCH$_2$CH$_2$N—), 4.04 (m, —COOCH$_2$—), 3.85 (m, —CH$_2$OP—), 3.67 (m, —POCH$_2$CH$_2$N—), 3.46 (m, —CHOH), 3.25 (s, —N(CH$_3$)$_3$), 2.65 (m, —CH$_2$-triazole in brush linker), 2.42-2.13 (m, cholesteric acid protons, brush linker protons), 2.10-0.85 (m, cholesteric acid protons, brush linker protons), 0.69 (s, —CH$_3$). $^{13}$C NMR (150 MHz, CD$_3$OD/CDCl$_3$): δ=174.81, 148.31, 140.90, 122.82, 121.32, 77.95, 71.13, 68.64, 66.35, 65.79, 64.46, 63.36, 58.86, 56.69, 55.73, 54.07, 50.77, 50.08, 42.31, 41.82, 39.70, 37.23, 36.44, 35.30, 31.84, 31.80, 31.24, 31.11, 30.99, 30.77, 29.50, 29.36, 29.25, 28.58, 28.03, 25.89, 25.77, 25.56, 24.17, 20.99, 19.23, 18.18, 11.74.

9. Preparation of Brush Polymer Compound (Example 5) (n=100)

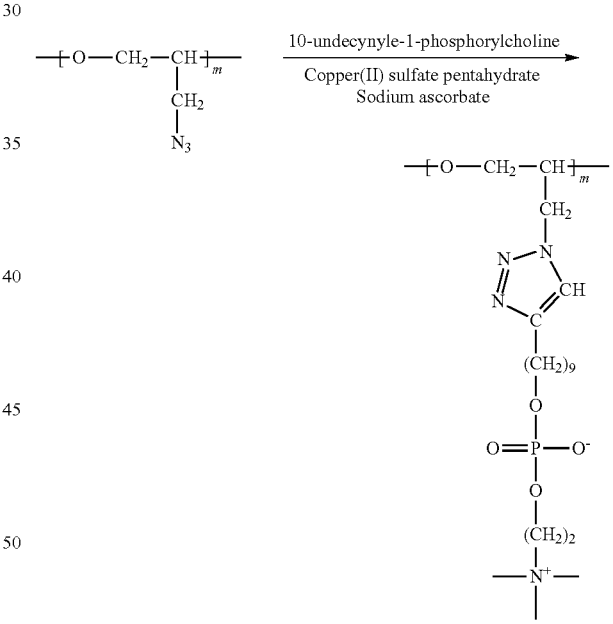

100 mg (1.00 N$_3$ mmol) of the polymer compound (PGA) obtained from Synthesis Example 2 was dissolved in a mixed solution (4 mL) of methanol and chloroform (1:3), and then 375 mg (1.00 mmol) of 10-undecynyl-1-phosphorylcholine was added thereto and dissolved. To this mixture were added 13 mg (5 mol %) of CuSO$_4$.5H$_2$O and 30 mg (15 mol %) of sodium ascorbate, and the mixture was stirred at room temperature for 48 hours. After the reaction was completed, the reaction product was purified through dialysis and then dissolved in a small amount of chloroform/methanol mixed solution and precipitated in cold diethyl ether. The resulting precipitate was collected through a filter and vacuum-dried to obtain a brush polymer compound. $^1$H NMR (300 MHz, CD$_3$OD/CDCl$_3$): δ=8.00-7.40 (br, 1H, —C=CH— in triazole), 4.50-3.10 (br, 5H, —CH$_2$CHO—, —CH$_2$CHO—, —CH$_2$-Triazole in backbone), 4.26 (m, 2H, —POCH$_2$CH$_2$N—), 3.85 (m, 2H, —CH$_2$OP—), 3.67 (m, 2H, —POCH$_2$CH$_2$N—), 3.25 (s, 9H, —N(CH$_3$)$_3$), 2.65 (m, 2H, —CH$_2$-triazole in brush linker), 1.90-0.85 (m, 14H, —(CH$_2$)$_7$—). $^{13}$C NMR (150 MHz, CD$_3$OD/CDCl$_3$): δ=148.09, 123.53, 77.79, 76.64, 70.21, 68.70, 66.06, 65.49, 58.97, 53.34, 50.91, 30.62, 29.43, 29.23, 25.65, 25.29.

10. Preparation of Polymer Thin Film

The brush polymeric compounds prepared in Examples 1 to 5 were dissolved in a mixed solvent of chloroform and methanol (50:50 vol %) at 1 wt %, and then filtered with a syringe filter of 0.2 microfilter. The solution filtered was spin-coated on the substrate and heat-treated at 50° C. for 12 hours under vacuum to prepare a polymer thin film. (If the above conditions are not met, it is difficult to form a nano-sized polymer thin film, and there may be problems in formation of nanostructure.)

Figure 2A:
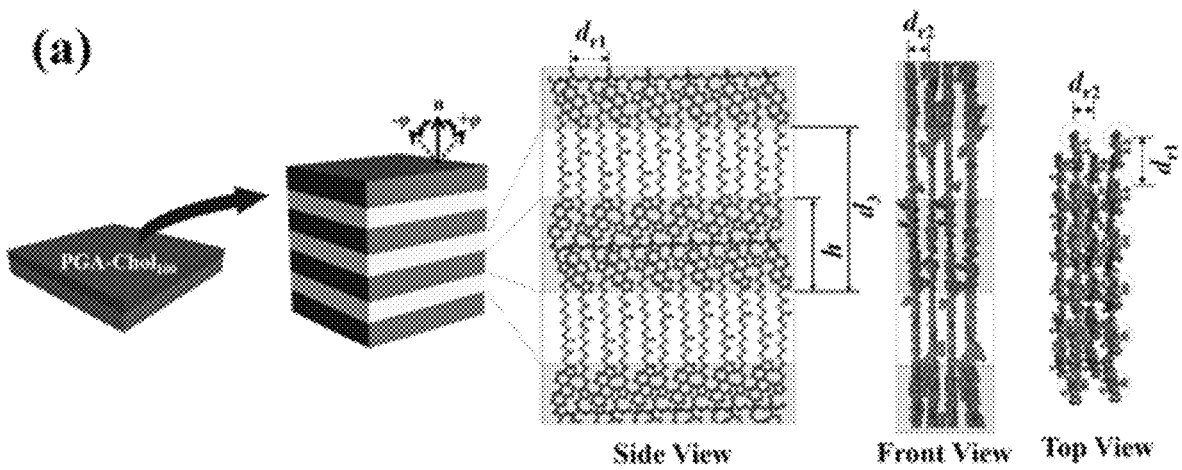
FIGS. 2A, 2B and 2C is schematic views showing a nanostructure of a polymer thin film according to an embodiment of the present invention.
Figure 2B:
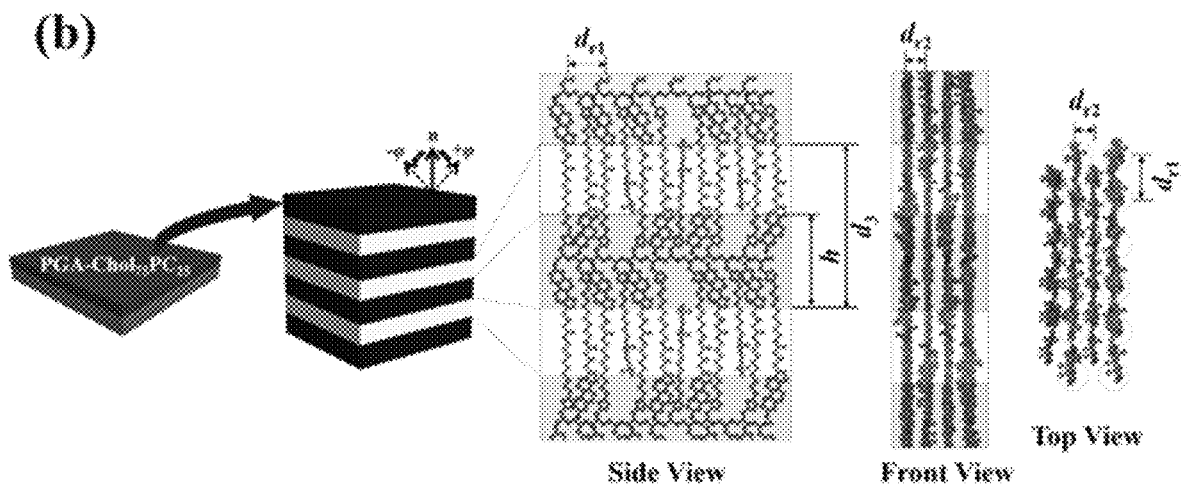
Figure 2C:
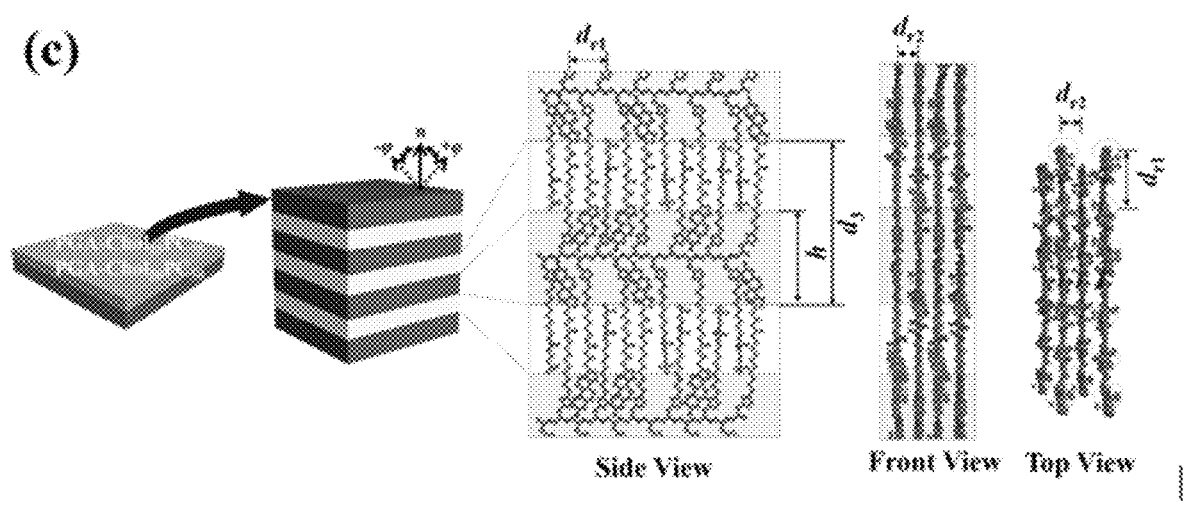
Figure 3:
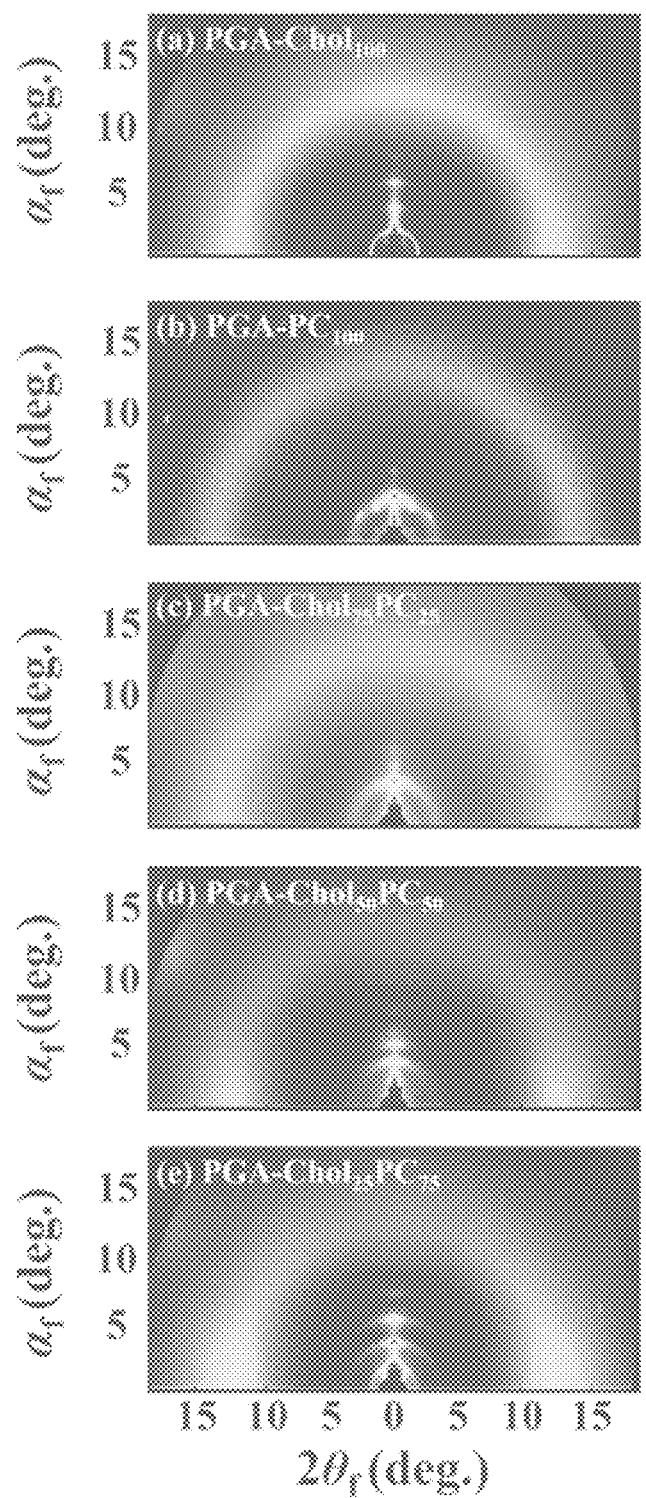
FIG. 3 is a GIWAXS image of a polymer thin film according to an embodiment of the present invention.

The nanostructure of the prepared polymer thin film is shown in FIG. 2, and the grazing incidence wide angle X-ray scattering (GIWAXS) pattern of a polymer thin film is shown in FIG. 3.

The structure of the thin film has a multibilayer structure (FIG. 2 (*a*)) at 100% according to the fraction of cholesterol terminal group, and as the fraction of phosphorylcholine terminal group increases, the steric hindrance caused by the triazole linker increases rather than the mutual attraction between the cholesterol terminal groups, and the brush tends to rotate, which interferes with the formation of the multibilayer structure. The optimum fraction for the multibilayer structure was evaluated as 75% of the cholesterol terminal group and 25% of the phosphorylcholine terminal group, which means that a certain percentage of the phosphorylcholine terminal group lowered the density of the bulky cholesterol terminal group to reduce steric hindrance. The h shown in FIG. 2 represents the thickness of the layer with a higher electron density in the multibilayer structure, dr1 denotes the distance between neighboring brushes connected to one main chain, and dr2 denotes the distance between adjacent main chains in the direction parallel to the thin film. FIG. 3 shows a two-dimensional scattering pattern of grazing incidence wide angle X-ray scattering, (a) shows a multibilayer structure of repeated patterns in a direction perpendicular to the thin film, and (b) shows a structure in which polymer chains lying in a direction parallel to a thin film are stacked in a cylindrical shape. The fraction of cholesterol terminal groups increased to 25%, 50%, and 75% from (c) to (e), and at 75%, scattering patterns are seen at regular intervals in the direction perpendicular to the film, which indicates that the multibilayer structure is best formed.

11. Protein Adsorption Experiment

Figure 4:
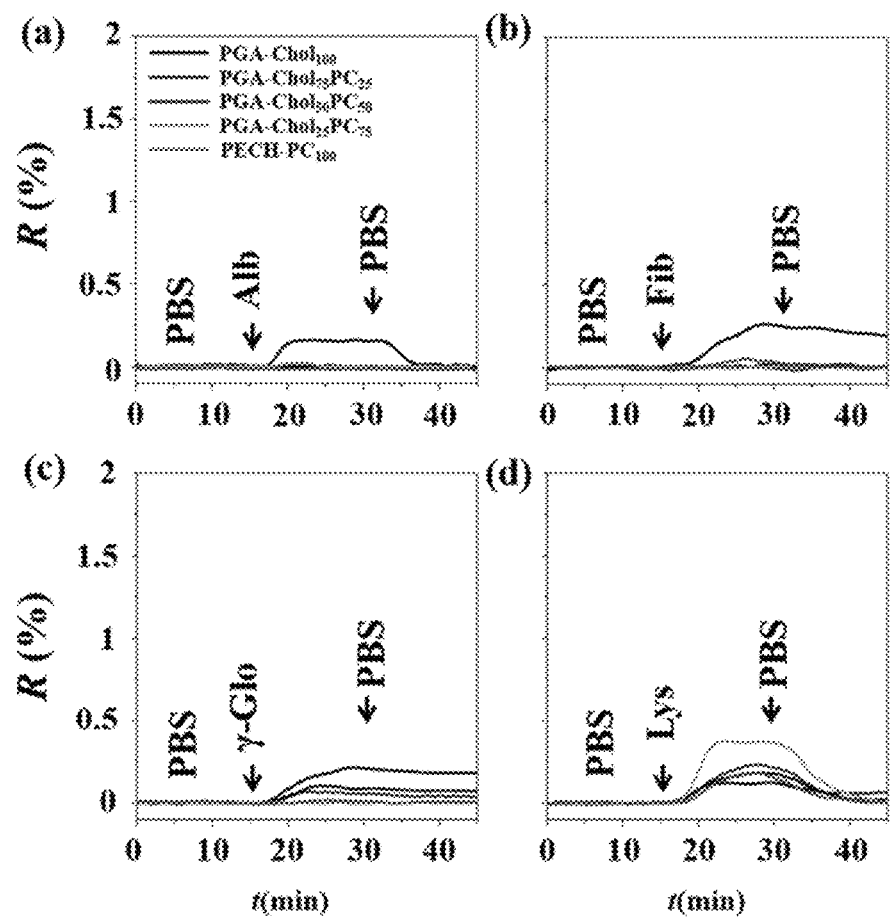
FIG. 4 is a graph showing protein adsorption using a surface plasmon resonance method of a polymer thin film according to an embodiment of the present invention.
Figure 5:
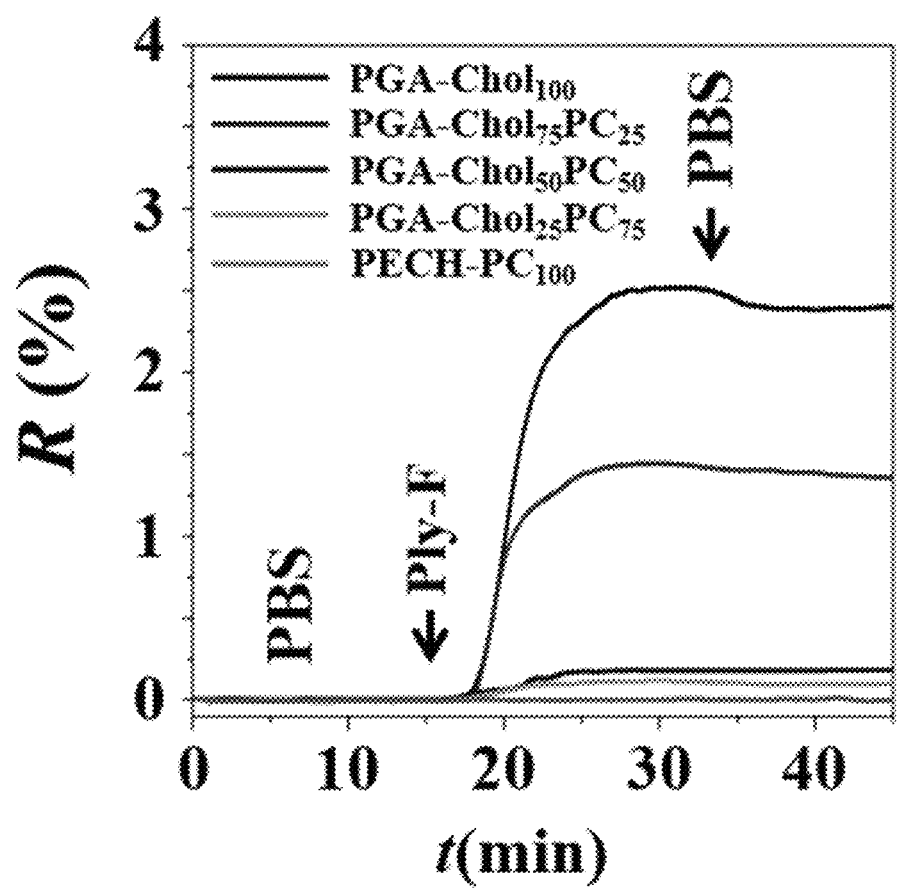
FIG. 5 is a graph showing pneumolysin adsorption using a surface plasmon resonance method of a polymer thin film according to an embodiment of the present invention.

The brush polymeric compounds prepared in Examples 1 to 5 were dissolved in a mixed solvent of chloroform and methanol (50:50 vol %) at 1 wt % and then filtered with a syringe filter of 0.2 microfilter. The solution filtered was then spin-coated on a prism coated with gold and heat-treated at 50° C. for 12 hours under vacuum. Polymer-coated prisms were tested for adsorption on four different proteins using surface plasmon resonance spectroscopy. The concentration of each protein was adjusted to 1 mg/mL, and the change in reflectance according to adsorption is shown in FIG. 4. The adsorption experiments of Pneumolysin were also carried out under the same conditions and are shown in FIG. 5.

What is claimed is:

1. A brush polymer compound comprising a structure represented by the following Formula 1:

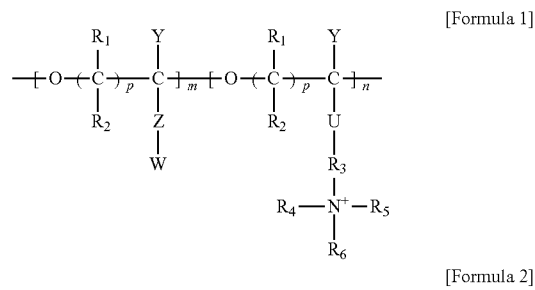

[Formula 1]

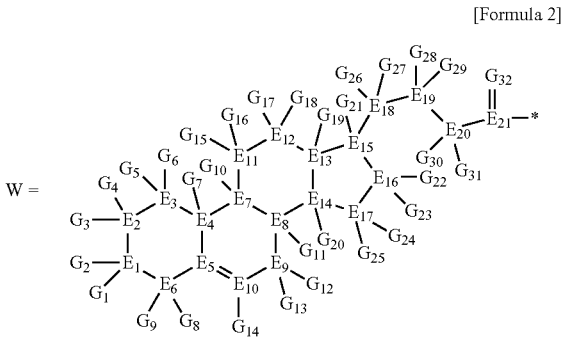

[Formula 2]

wherein,

R$_1$, R$_2$, R$_4$, R$_5$ and R$_6$ are independently hydrogen or an alkyl group having 1 to 20 carbon atoms; R$_3$ is an alkylene having 1 to 20 carbon atoms; ρ is an integer of 0 to 20; m and n represent the content (mol %) of the polyether unit, 0≤m≤100, 0≤n≤100 and m+n=100;

Y is H, —CH$_2$X (wherein X is F, Cl, Br or I), an alkyl group having 1 to 20 carbon atoms, UR$_3$N$^⊕$[R$_4$R$_5$R$_6$] or —ZW;

Z and U are linkers connecting the terminal functional group and the polyether backbone;

W is a carbocyclic group of the Formula 2 comprising E$_1$ to E$_{21}$ and G$_1$ to G$_{32}$;

-* represents the point to be connected to Z;

E$_1$ to E$_{21}$ are independently selected from the group consisting of C, N, O, P and S;

provided that E$_4$, E$_5$, E$_7$, E$_8$, E$_{10}$, E$_{13}$, E$_{14}$ and E$_{15}$ are not O and S;

when any one of E$_1$ to E$_{21}$ is O or S, G attached thereto is not present;

when any one of E$_1$ to E$_{21}$ is N or P, there is no or at most one G attached thereto;

G$_1$ to G$_{32}$, when present, are independently selected from the group consisting of —CHO, COOH, —H, —N$_3$, —NO$_2$, —NH$_2$, —OH, —PO$_3$H, —SH, —SO$_3$H, —CH$_3$, —C$_6$H$_5$ and alkyl group having 1 to 20 carbon atoms, or together form =O, =N or =S with two G's connected to the same E.

2. The brush polymer compound according to claim 1, wherein Z and U are independently selected from the group represented by the following Formula 3:

[Formula 3]
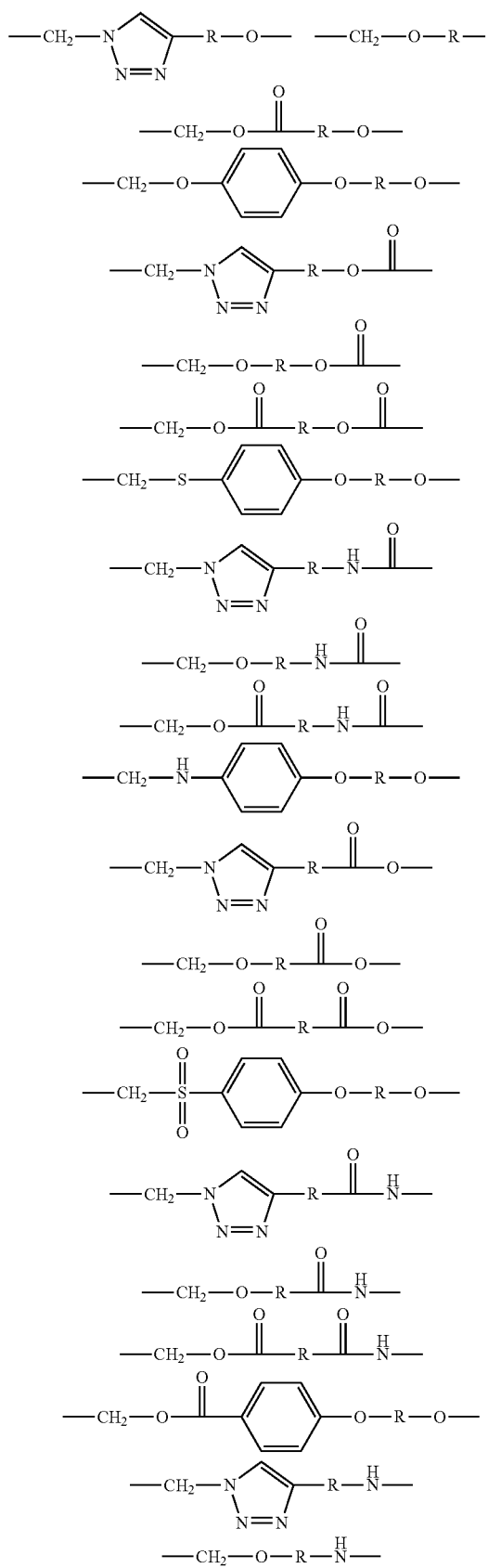
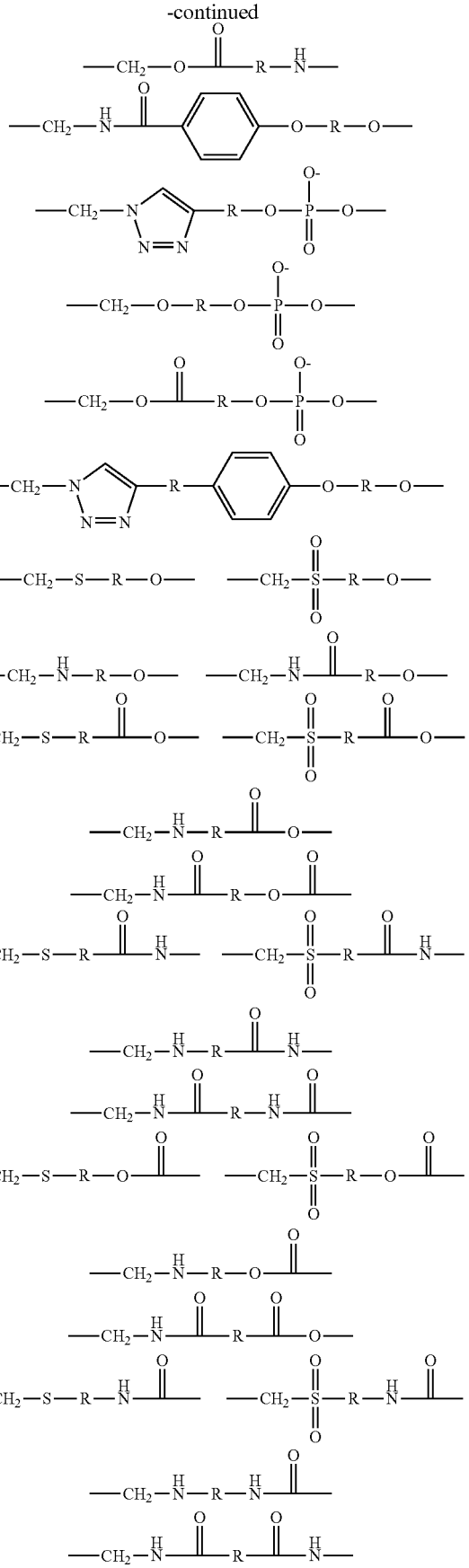

-continued

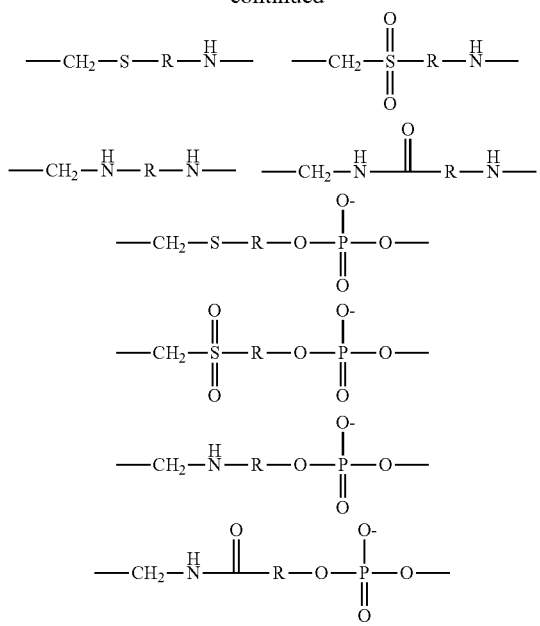

wherein R is hydrogen or an alkylene group having 1 to 20 carbon atoms.

3. The brush polymer compound according to claim 1, having a weight average molecular weight of 5,000 to 5,000,000.

4. The brush polymer compound according to claim 1, comprising a structure represented by the following Formula 4:

[Formula 4]

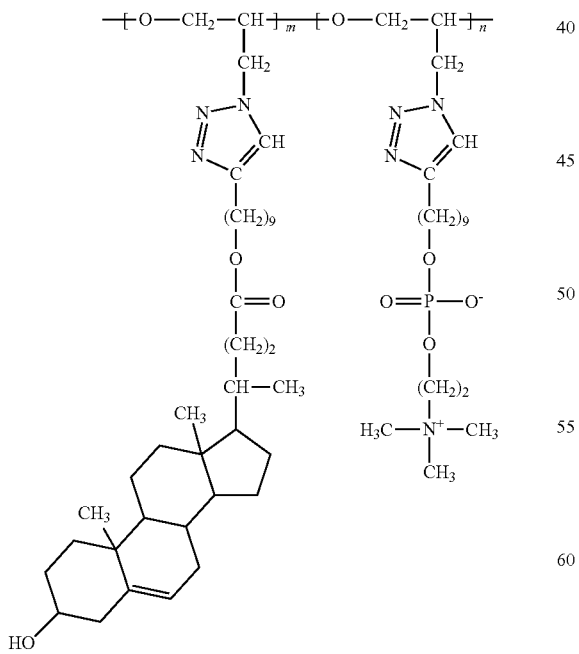

wherein m and n represent the content (mol %) of the polyether unit, $0 \leq m \leq 100$, $0 \leq n \leq 100$ and $m+n=100$.

5. A method for preparing a brush polymer compound, comprising the steps of:

step (1) of preparing a polyether polymer compound comprising a structure represented by the Formula 6 from the cyclic monomers of the Formula 5 through cationic ring-opening polymerization, step (2) of preparing a polymer compound having an azide group and comprising a structure represented by the Formula 7 from the polyether polymer comprising the structure of the Formula 6 in the step (1) through a halogen substitution reaction in an organic solvent and step (3) of preparing a brush polymer compound of the Formula 1 using the azide group of the polymer compound having an azide group of the step (2) and the cycloaddition reaction of the alkyne group of the functional molecule:

[Formula 5]

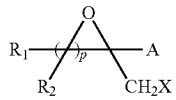

[Formula 6]

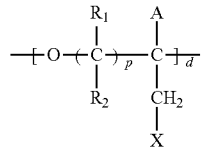

in the Formulas 5 and 6, $R_1$ and $R_2$ are hydrogen or an alkyl group having 1 to 20 carbon atoms, $\rho$ is an integer of 0 to 20, d is 50 to 50,000, A is hydrogen, an alkyl group having 1 to 20 carbon atoms or —$CH_2X$ (wherein X is F, Cl, Br or I),

[Formula 7]

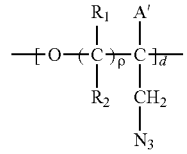

in the Formula 7, $R_1$ and $R_2$ are hydrogen or an alkyl group having 1 to 20 carbon atoms, $\rho$ is an integer of 0 to 20, d is 50 to 50,000 and A' is H, —$CH_2N_3$ or an alkyl group having 1 to 20 carbon atoms,

[Formula 1]

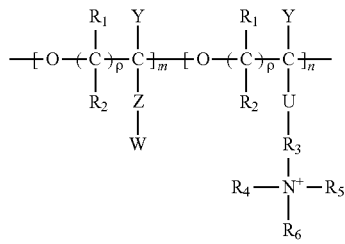

-continued

[Formula 2]

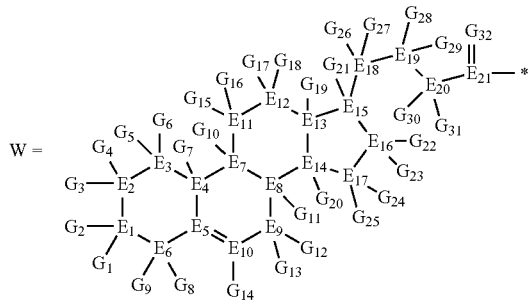

wherein,
$R_1$, $R_2$, $R_4$, $R_5$ and $R_6$ are independently hydrogen or an alkyl group having 1 to 20 carbon atoms; $R_3$ is an alkylene having 1 to 20 carbon atoms; $\rho$ is an integer of 0 to 20; m and n represent the content (mol %) of the polyether unit, $0 \leq m \leq 100$, $0 \leq n \leq 100$ and $m+n=100$;

Y is H, —$CH_2X$ (wherein X is F, Cl, Br or I), an alkyl group having 1 to 20 carbon atoms, $UR_3N^{⊕}[R_4R_5R_6]$ or —ZW;

Z and U are linkers connecting the terminal functional group and the polyether backbone;

W is a carbocyclic group of the Formula 2 comprising $E_1$ to $E_{21}$ and $G_1$ to $G_{32}$;

-* represents the point to be connected to Z;

$E_1$ to $E_{21}$ are independently selected from the group consisting of C, N, O, P and S;

provided that $E_4$, $E_5$, $E_7$, $E_8$, $E_{10}$, $E_{13}$, $E_{14}$ and $E_{15}$ are not O and S;

when any one of $E_1$ to $E_{21}$ is O or S, G attached thereto is not present;

when any one of $E_1$ to $E_{21}$ is N or P, there is no or at most one G attached thereto;

$G_1$ to $G_{32}$, when present, are independently selected from the group consisting of —CHO, COOH, —H, —$N_3$, —$NO_2$, —$NH_2$, —OH, —$PO_3H$, —SH, —$SO_3H$, —$CH_3$, —$C_6H_5$ and alkyl group having 1 to 20 carbon atoms, or together form =O, =N or =S with two G's connected to the same E; and the functional molecule comprises $UR_3N^{⊕}[R_4R_5R_6]$ or —ZW at either end, and comprises an alkyne group at the opposite end.

6. A polymer thin film comprising the brush polymer compound according to claim 1.

7. A method for preparing a polymer thin film, which comprises a step of coating a brush polymer compound of claim 1 on a substrate.

8. The method for preparing a polymer thin film according to claim 7, wherein the coating is performed by any one method selected from the group consisting of spin coating, spray coating, electrostatic coating, dip coating, blade coating, ink jet coating and roll coating.

9. The method according to claim 7, comprising a step of heat treating the substrate coated with the brush polymer compound under vacuum at 30 to 100° C. for 10 to 20 hours.

* * * * *